(12) United States Patent
Roberts

(10) Patent No.: US 10,203,314 B2
(45) Date of Patent: Feb. 12, 2019

(54) METHOD FOR CALCULATING FEED VALUE OF ALFALFA HAY USING INFORMATION AVAILABLE AT TIME OF BALING

(71) Applicant: Jeffrey S. Roberts, Hudson, WI (US)

(72) Inventor: Jeffrey S. Roberts, Hudson, WI (US)

(73) Assignee: Harvest Tec, Inc., Hudson, WI (US)

( * ) Notice: Subject to any disclaimer, the term of this patent is extended or adjusted under 35 U.S.C. 154(b) by 0 days.

(21) Appl. No.: 15/496,734

(22) Filed: Apr. 25, 2017

(65) Prior Publication Data

US 2017/0284988 A1 Oct. 5, 2017

Related U.S. Application Data

(63) Continuation-in-part of application No. 13/573,461, filed on Sep. 17, 2012, now Pat. No. 9,632,070.

(51) Int. Cl.
G01N 33/02 (2006.01)
A23K 50/10 (2016.01)
G06F 17/00 (2006.01)
G01N 33/00 (2006.01)

(52) U.S. Cl.
CPC ............ *G01N 33/02* (2013.01); *A23K 50/10* (2016.05); *G01N 33/00* (2013.01); *G06F 17/00* (2013.01)

(58) Field of Classification Search
CPC .......... G01N 33/02; A23K 50/10; G06F 17/00
See application file for complete search history.

(56) References Cited

U.S. PATENT DOCUMENTS

| 4,885,531 | A | * | 12/1989 | Stowell | G01N 27/048 324/695 |
|---|---|---|---|---|---|
| 5,226,356 | A | * | 7/1993 | Schrag | B30B 9/3025 100/41 |
| 5,253,570 | A | * | 10/1993 | Goeckner | A01F 15/0825 100/191 |
| 6,088,657 | A | * | 7/2000 | McMahon | G01N 27/4166 324/694 |
| 6,377,058 | B1 | * | 4/2002 | Pemrick | A01F 15/08 324/694 |
| 2005/0210699 | A1 | * | 9/2005 | Philippe | A01F 25/08 34/191 |
| 2012/0186465 | A1 | * | 7/2012 | Dresher | A01F 15/101 100/35 |

* cited by examiner

*Primary Examiner* — John Breene
*Assistant Examiner* — Yaritza H Perez Bermudez
(74) *Attorney, Agent, or Firm* — Skinner and Associates; Joel Skinner

(57) ABSTRACT

A method where the weight of the bale is measured by a scale on the baler, the moisture of the bale is measured by sensors on the baler and this information is sent to a processor. Based on compaction properties of the leaf verses the stem of the alfalfa, the processor calculates a feeding value for the hay including protein, energy and relative feed value on the dry density of the bale. Additional inputs such as the compaction setting of the baler and information about the hay being harvested can also be input into the processor for making adjustment to the feeding value calculation.

12 Claims, 3 Drawing Sheets

METHOD FOR CALCULATING FEED VALUE OF ALFALFA HAY USING INFORMATION AVAILABLE AT TIME OF BALING

CROSS REFERENCE TO RELATED APPLICATIONS

A System and method for identifying bales of hay, U.S. Pat. No. 7,415,924 B2.

A System and Method for identifying Bales of Hay, U.S. Pat. No. 7,621,111 B2.

THE NAMES OF PARTIES ON A JOINT RESEARCH AGREEMENT

Not Applicable.

STATEMENT REGARDING FEDERALLY SPONSORED RESEARCH FOR DEVELOPMENT

Not Applicable.

BACKGROUND

Alfalfa hay is a primary source of feed for dairy and beef feeding operations. While growing, the alfalfa plant is approximately fifty percent leaves and fifty percent stems. Ninety percent of the feeding value, including protein and relative feed value is in the leaf portion of the plant. The feeding value of alfalfa will vary depending on how it is harvested and the resulting ratio of leaves to stems in the harvested alfalfa crop as the leaves will separate from the stems as it is mechanically handled. The common practice of feeders of alfalfa is to pull samples of the harvested alfalfa and send them into a lab to determine the feeding value, so that the ration fed to dairy and beef livestock can he adjusted with other supplements to feed the correct amount of nutrients to produce milk or meat.

One of the main methods for harvesting alfalfa is to use a hay baler, harvesting the alfalfa under sixteen percent moisture content so that the alfalfa does not spoil due to a higher moisture. As the alfalfa dries, it becomes difficult to keep the leaves on the plant as it is baled and the leaves are separated from the stem with the mechanical action of the baler. When baling at sixteen percent moisture, the finished bale will be approximately forty percent leaves and sixty percent stems as the mechanical action of the baler separates some of the leaves. When the hay dries from sixteen down to thirteen percent moisture, additional leaves are separated during baling o the finished bale will be thirty percent leaves and sixty percent stems. This change in the leave to stem ratio leads to a significant reduction in the feeding quality. Multiple tests for the feeding quality are required to identify the different levels of nutrient value between bales due to variation of the moisture at harvest.

Recently, balers have been common equipped with a scale device to weigh the bales being made. The leaf portion of the alfalfa plant which is flat will compress to a higher density than the stem portion of the plant which is round Tests run on alfalfa samples at 16% moisture in a compression chamber with six hundred pounds per square inch of pressure applied, which is similar to the compression applied during baling, illustrate how the properties of compression are influences by ratio of leaves and stems as follows:

| % LEAVES | % STEMS | BALE WEIGHT | BALE VOLUME (3 FT × 3 FT × 8 FT BALE) | DENSITY OF SAMPLES (POUNDS PER SQ FOOT) |
| --- | --- | --- | --- | --- |
| 100% | 0% | 1440 POUNDS | 72 CU FT | 20 pounds |
| 80% | 20% | 1296 POUNDS | 72 CU FT | 18 pounds |
| 60% | 40% | 1152 POUNDS | 72 CU FT | 16 pounds |
| 50% | 50% | 1080 POUNDS | 72 CU FT | 15 pounds |
| 40% | 60% | 1008 POUNDS | 72 CU FT | 14 pounds |
| 30% | 70% | 936 POUNDS | 72 CU FT | 13 pounds |
| 20% | 80% | 864 POUNDS | 72 CU FT | 12 pounds |
| 10% | 90% | 720 POUNDS | 72 CU FT | 10 pounds |
| 0% | 100% | 576 POUNDS | | |

Ninety percent of the feeding value of alfalfa is in the leaf portion of the plant. As the leaf to stem ratio changes, the feeding value of the alfalfa also changes as measured by two important values of the feeding quality, protein and relative feed value (RFV). Feeding quality tests run on alfalfa samples at 16% moisture with various leaf to stem ratios show the following values:

| | | TESTED FEED QUALITY | |
| --- | --- | --- | --- |
| % LEAVES | % STEMS | PROTEIN | RELATIVE FEED VALUE |
| 100% | 0% | 28% | 240 |
| 80% | 20% | 26% | 220 |
| 60% | 40% | 24% | 200 |
| 50% | 50% | 23% | 190 |
| 40% | 60% | 22% | 180 |
| 30% | 70% | 20% | 160 |
| 20% | 80% | 16% | 120 |
| 10% | 90% | 14% | 100 |
| 0% | 100% | 12% | 80 |

Recently, balers have been equipped with moisture sensors. As moisture is added to a bale of hay, the Weight of the bale changes, due to the weight of the water within the bale. A test of a bale fourteen inches by sixteen inches by thirty-six inches (4.66 cubic feet) demonstrate the change in weight as water is added to the bale:

| % moisture content | bale weight |
| --- | --- |
| 10% | 46.6 pounds |
| 12% | 47.5 pounds |
| 14% | 48.5 pounds |
| 16% | 49.6 pounds |
| 18% | 50.7 pounds |
| 20% | 51.8 pounds |
| 22% | 53.0 pounds |

In the method that has been invented, factoring in the moisture of the bale to the weight of the bale, gives an estimate of the leaf to stem ratio and therefore a method for calculating its feeding value.

BRIEF SUMMARY OF THE INVENTION

In the method that has been invented, the weight of the bale is measured by a scale on the baler, the moisture of the bale is measured by sensors on the baler and this information is sent to a processor. Based on compaction properties of the leaf verses the stem of the alfalfa, the processor calculates a feeding value for the hay including protein, energy and relative feed value on the dry density of the bale. Additional inputs such as the compaction setting of the baler and information about the hay being harvested can also be input into the processor for making adjustment to the feeding value calculation.

DETAILED DESCRIPTION OF THE INVENTION

Figure 1:
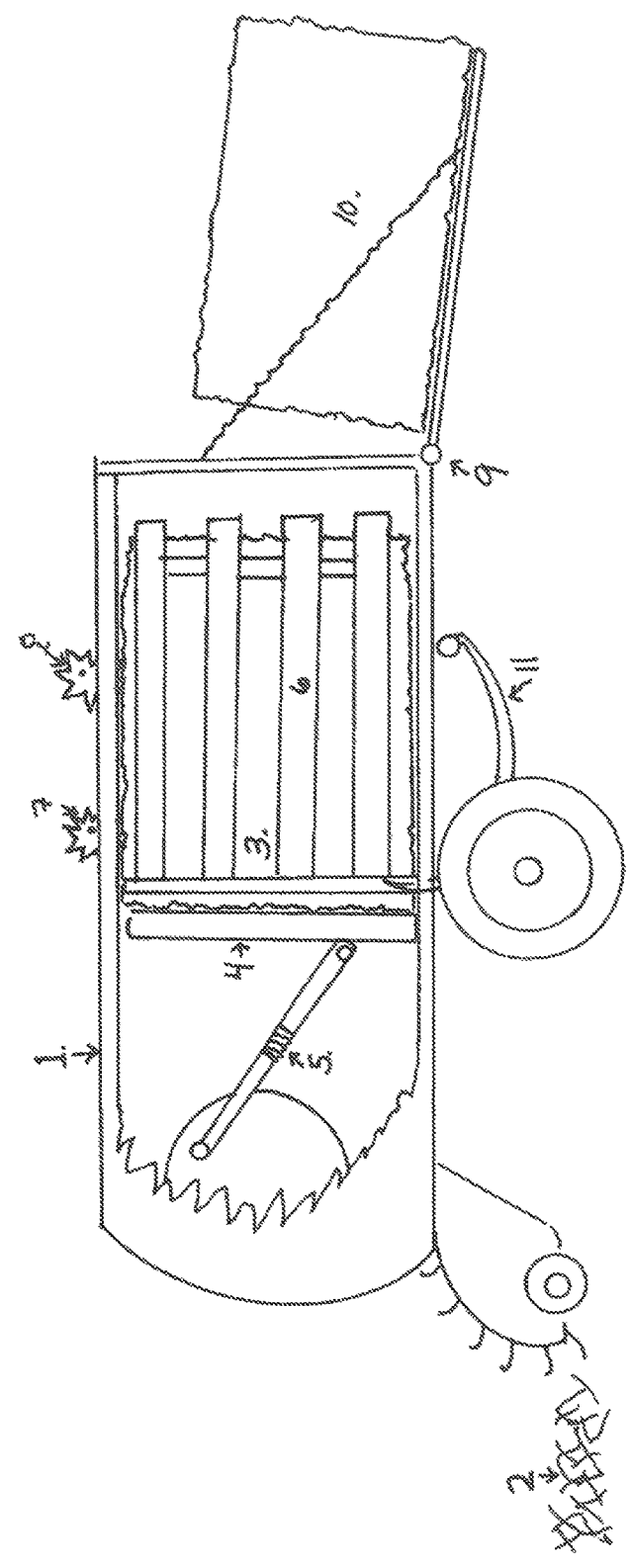
FIG. 1 shows a baler with the weighing system, moisture testing system and compaction system.
Figure 2:
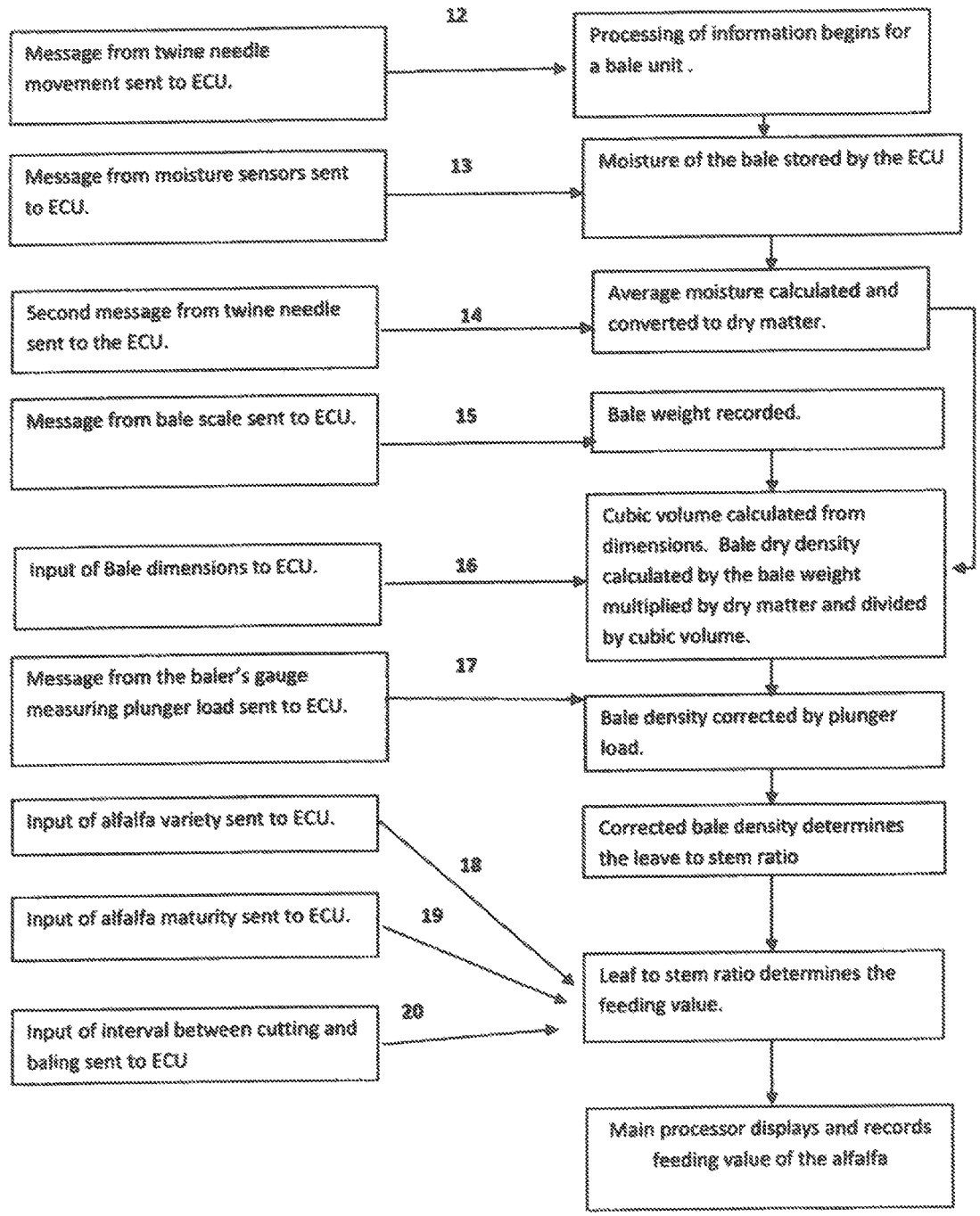
FIG. 2 shows a flow chart of the processing of inputs from the baler to predict feeding quality.

A hay baler 1 Picks up alfalfa from a windrow 2 to form a bale 1. The baler's plunger mechanism 4 compacts the bale and a gauge 5 senses the load of compaction from the plunger. The plunger pressure against the hay is regulated by increasing or decreasing the size of the chamber by setting the position of the doors 6 to squeeze the hay into a fixed area. The moisture of the bale is read by conductivity between two metal star wheels 7 and 8 on the formed bale 3. As the bale is delivered out of the baler, it is weighed by a scale device picking up signals from load cells at critical points 9. The bale weight is read on a completely formed bale 10 that is separated from the previous bale 3 as it is delivered from the baler to get an isolated reading from the load cells 9. A needle 11 routes the twine which holds the individual bales together and its movement is sensed in this method to identify each bale as a contiguous unit.

To calculate the feeding value of the bale of alfalfa, information is received from the weight and moisture sensors on the baler and processed by an electronic control unit (ECU). In the memory of the ECU, a table of feeding quality is stored for the protein, relative feed value and other related quality measurements based on the dry density of alfalfa hay. The steps in the processing begin with the needle 11 sending a message to the ECU 12 when it moves signaling that the twine has been routed up through the hay defining the start of the bale. Readings for percent moisture from the moisture sensors 7 and are sent to the ECU 13 and stored in the ECU until the next message from the twine needle is received 14 signaling the end of the bale. After receiving that message the ECU calculates average moisture for the bale formed between the two movements of the needle. The ECU converts the moisture reading to a dry minter value by subtracting the moisture percent from one hundred percent.

When the bale moves to a position 10, the bale scale 9 will see an increase in weight readings as the portion of the bale resting in the scale increases. When this weight reaches a maximum, the bale scale reading sent to the ECU 15 is recorded as the weight of the bale.

A means for inputting the dimension of the bale is provided to the ECU 15. The cubic volume of the bale is calculated from these dimensions by the ECU. The ECU uses the bale weight multiplied by the dry matter percent and divides that by the cubic volume to calculate a dry density of the bale. The ECU then compares the corrected dry density of the bale to a look up table in memory and displays and records the feed value for the bale.

The load reading for the baler's load sensor 5 can be sent to the ECU 17 to correct the density calculated. The ECU then compares the corrected dry density to a look-up table stored in the memory of the ECU, and records and displays a feed value for the bale.

Further corrections can be input into the ECU. Some plant varieties of alfalfa are higher in feed value than others. Correction factors can be input into the ECU 18 for known varieties of alfalfa and a selection of those varieties sent to the ECU which corrects the displayed and recorded feed value.

Maturity of the alfalfa at harvest can affect feeding value. Correction factors an be input into the ECU 19 for a selection of maturities of the alfalfa. A selection of maturities can be sent to the ECU and the feeding values can be corrected for the displayed and recorded feed values.

The interval between cutting and baling can also affect the feeding value of the alfalfa. Correction factors for the hours of time between cutting and baling can be input into the ECU 20. A selection of hours between cutting and baling can he sent to the ECU which corrects the displayed and recorded feed value.

Figure 3:
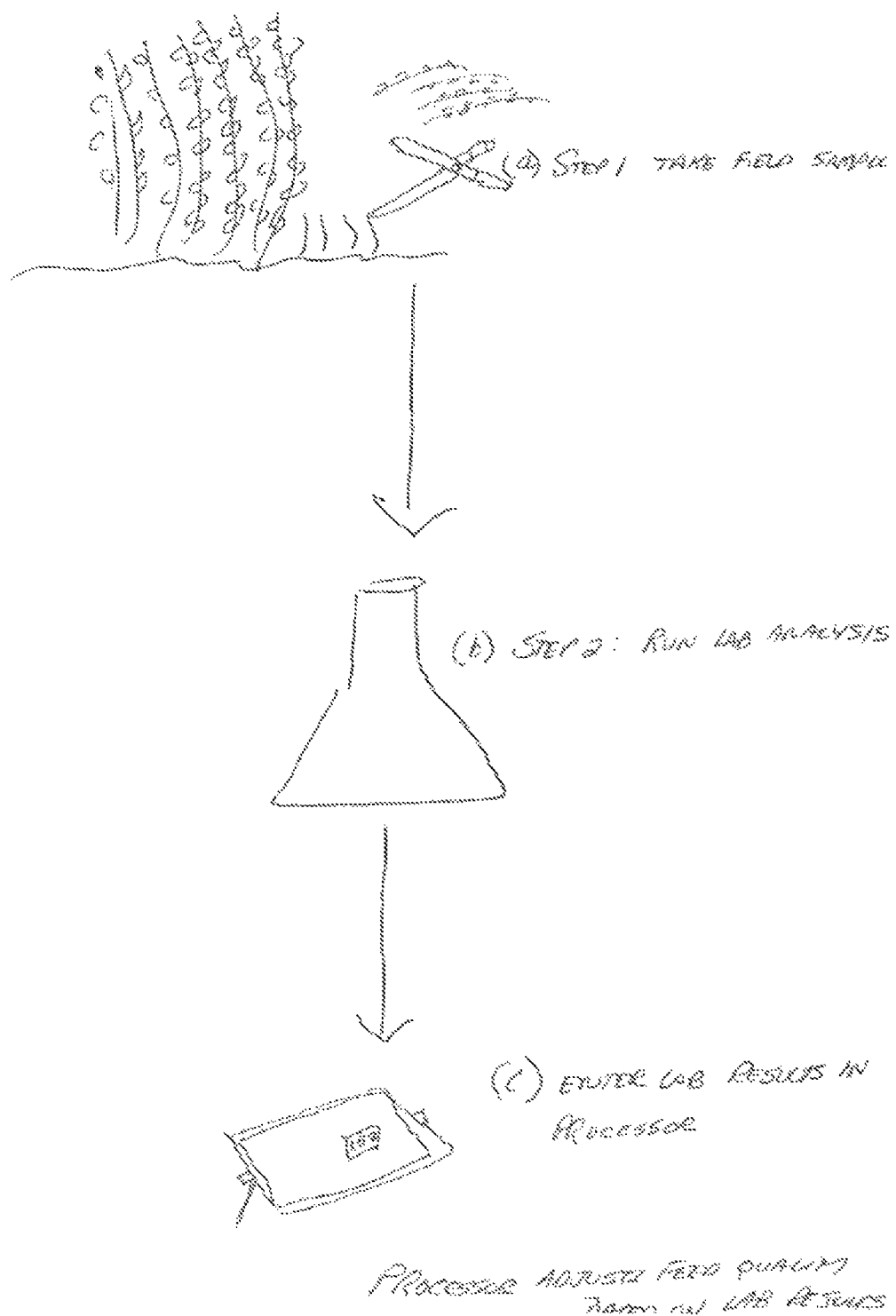
FIG. 3 illustrates an optional further step in the method of the invention.

FIG. 3 shows an optional, additional system and sub process of the basic device and method of the invention. The addition involves obtaining a physical sample of hay from the field being harvested prior to processing, analyzing that pre-sample chemically to determine the nutrient value, and using that value during normal processing. This may be done in one of two ways:

1. Manually pull samples just before or after the crop is cut, analyze them in a lab, and enter the analyzed feed value into the processor as a starting point for making the calculation while baling; and
2. Measure the standing value of the crop with instrumentation on the baler or cutting implement.

The cutting implement may send that information to the baler and input that based on GPS position into the system that would then follow the base method described above. Both methods liter the pre-sampled value into the processor. The embodiments above are chosen, describe and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application tempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act based equivalents and equivalent acts.

What is claimed:

1. A method for determining the nutritional feed value of alfalfa hay in a bale being baled by a baler, based on the ratio of leaves to stems, comprising the steps of:
   providing a baler including a scale, a moisture sensor, a processor connected to the scale and moisture sensor, and a display connected to the processor;
   measuring the weight of a bale, of a predetermined size, of alfalfa using the scale;

measuring the moisture of the bale of alfalfa using the moisture sensor;

manually pulling samples just before or after the crop is cut;

chemically analyzing the manually pulled sample to obtain a first feed quality value:

calculating, by the processor, a dry density of the bale based on the measured weight of the bale;

comparing, by the processor, the dry density of the bale to a table of values for feeding quality, as a function of the ratio of leaves to stems, based on dry density stored in a memory of the processor;

entering the first feed quality value from the chemical analysis into the processor, where the values for feeding quality on the table are adjusted up or down based on the value of that of that first feed quality value;

recording a feed value; and displaying the feed value on the display.

2. The method of claim 1, wherein the baler further includes a hay pickup, a plunger mechanism, a bale forming area, and a bale output, wherein the plunger is communicatively connected to the bale forming area, and further comprising a load sensor communicatively connected to the plunger, and where force of compaction is read from the load sensor and used to further correct the feed value recorded and displayed.

3. The method of claim 2 where a variety of alfalfa is entered into the processor and used to further correct the feed value recorded and displayed.

4. The method of claim 2 where a maturity of the alfalfa is entered into the processor arid used to further correct the feed value recorded and displayed.

5. The method of claim 2 where a time interval between cutting of the alfalfa and baling of the alfalfa is entered into the processor and used to farther correct the feed value recorded and displayed.

6. The baler apparatus of claim 2, wherein the moisture sensor includes at least two conductivity star wheels.

7. The method of claim 2, wherein the baler further comprises a twine router communicatively connected to the processor to determine the start and end of bale forming cycle.

8. The method of claim 1, wherein the baler includes a hay pickup, a plunger mechanism, a bale forming area, and a bale output, wherein a time interval between cutting of the alfalfa and baling of the alfalfa is entered into the processor and used to further correct the feed value recorded and displayed.

9. The method of claim 1, further comprising the steps of (a) taking a representative pre-sample of the crop, (b) obtaining a first feed value in a laboratory of the pre-sample, and (c) entering the first feed value into the processor where the value for feeding quality on the table are adjusted up or down based on tile value of that first feed quality.

10. The method of claim 1, further comprising the step of (a) measuring the standing value of the crop with instrumentation on a cutting implement (b) chemically analyzing the crop sample to obtain a first feed quality value, and (c) entering that first feed quality value from the chemical analysis into the processor, where the values for feeding quality on the table are adjusted up or down based on the value of that of that first feed quality.

11. The method of claim 1, further comprising the step of (a) measuring the standing value of the crop with instrumentation on a cutting implement (b) chemically analyzing the crop sample to obtain a first feed quality value, and (c) electronically communicating the first feed quality value from the cutting implement to the processor where the values for feeding quality on the table are adjusted up or down based on the value of that first feed quality value.

12. The method of claim 1, further comprising the steps of (a) measuring the height of the crop and comparing that height to a known approximate relationship of crop height to first feed quality, and (b) entering the approximate first feed quality value into the processor where the values for feeding quality on the table are adjusted up or down based on the value of that first feed quality.

* * * * *